May 19, 1953 F. MEILLAND Plant Pat. 1,188
ROSE PLANT
Filed June 11, 1952
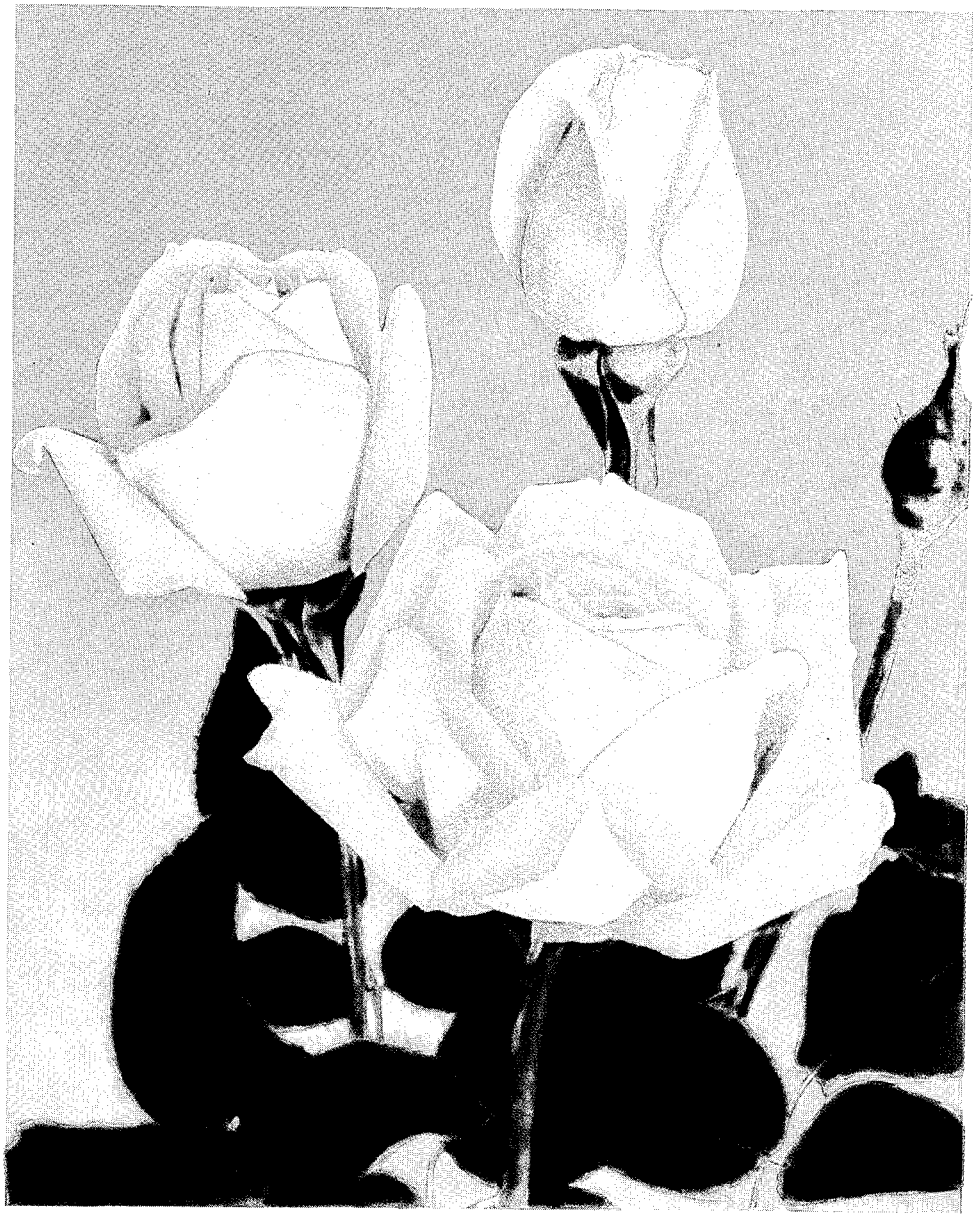
Inventor
Francis Meilland
By: Robert Cobb
Attorneys.

Patented May 19, 1953

Plant Pat. 1,188

UNITED STATES PATENT OFFICE 1,188

ROSE PLANT

Francis Meilland, Cap Azura, Cap d'Antibes, France, assignor to The Conard-Pyle Company, West Grove, Pa., a corporation of Pennsylvania Application June 11, 1952, Serial No. 293,030
In France September 24, 1951

1 Claim. (Cl. 47—61)

The present invention relates to a new and distinct variety of rose plant of the hybrid tea class, originated by me by crossing the variety "Peace," known as "Mme. A. Meilland" in France (Plant Patent No. 591), with the variety "J. B. Meilland" (unpatented).

The primary objective in making this cross was to produce a new and improved hybrid tea rose of a red and yellow bi-color type in vivid, lively, yet harmonious shades of color, on a plant of more vegetative vigor with good disease resistance than any varieties previously known in this light, bright range of bi-colored roses.

This objective was fully achieved, as evidenced by the fact that my new variety produces bright and attractive flowers of the red and yellow bi-color range, as hereinafter more fully described in detail and as more particularly illustrated in the accompanying drawing; the foliage on the plant of my new variety is unusually handsome, and the improved vigor of the plant is expressed in its bushy growth, abundance of foliage produced, and great freedom of bloom. The combination of these characteristics represents a significant and important advance in hybrid tea rose varieties of the bi-color type, and clearly distinguishes my new variety from its parents, as well as from all other varieties of which I am aware.

Asexual reproduction of my new variety by buddings both at Tassin-les-Lyon, France, and at West Grove, Pennsylvania, U. S. A., shows that the foregoing characteristics and distinctions come true to form and are established and transmitted through succeeding propagations.

The accompanying drawing shows specimens of my new variety, with the flowers and foliage in different stages of development, and with the colors depicted in the drawing as nearly true as it is reasonably possible to make the same in an illustration of this character.

The following is a detailed description of my new variety, with color terminology in accordance with Ridgway's Color Standards and Nomenclature, except where general color terminology of ordinary dictionary significance is obvious:

Type: Hardy; bush; outdoor; seedling; for cut flowers and for garden decoration.
Class: Hybrid tea.
Breeding: Seedling.
*Seed parent.*—"Peace."
*Pollen parent.*—"J. B. Meilland."
Propagation: Holds its distinguishing characteristics through succeeding propagations by budding.

*Flower*

Locality where grown and observed: West Grove, Pennsylvania, U. S. A.

Flowers borne: Singly to stem; on strong, medium length stems.
Quantity of bloom: Free, outdoors.
Continuity: Continuous.
Fragrance: Light in type; moderately strong.
Bud:
*Peduncle.*—Medium length; medium weight; medium green; medium rough; a number of small colorless prickles.
*Before calyx breaks.* — Size — medium. Form—short; ovoid; with foliaceous parts extending beyond the tip of the bud equal to ½ or more of its length.
*As calyx breaks.* — Color — Light Greenish Yellow, Plate V, tinged Jasper Red, Plate XIII.
*As first petal opens.*—Size—medium. Form—medium short pointed; globular. Color—outside—Apricot Yellow, Plate IV, at base, to Cadmium Yellow, Plate IV, with outside border suffused with Scarlet, Plate 1. Inside—Scarlet-Red, Plate I, with small, well-defined base of shining Light Cadmium, Plate IV.
*Opening.*—Opens up well.
Bloom:
*Size, when fully open.*—Medium; 3¾ inches to 4¾ inches or more.
*Petalage.*—Double; from 30 to 45 petals; arranged irregularly.
*Form.*—Cupped at first; at maturity, each outer petal becomes rolled outward to a pointed, cone shape; toward the center of the flower, petals show progressively less of this outward roll; innermost petals are waved or cupped.
Petals: Medium thick; leathery; with inside satiny with velvety yellow base, and outside velvety.
*Shape.*—Outer—obovate, with apex almost flat with two slight, shallow notches. Intermediate—obovate, with apex practically flat; with two slight to imperceptible notches. Inner—obovate, with apex almost flat; with two almost imperceptible notches.

This description of a newly opened flower was made from a rose grown in a greenhouse in the month of March, at West Grove, Pennsylvania, U. S. A.:

*Color.*—Outer petal—outside surface: Base Lemon Yellow, Plate IV, to Lemon Chrome, Plate IV, to Buff-Yellow, Plate IV, to an outer zone that is gradually stained Light Jasper Red, Plate XIII, darkening to Jasper Red, Plate XIII, at the outer edge; inside surface: small, well-defined base of Lemon Chrome, Plate IV. Most of the petal is a very bright Rose Red, Plate XII, tending toward Spectrum Red, Plate I, toward the base of the petal. Intermediate petal—outside surface: Lemon Yellow, Plate IV, at base, shading to Baryta Yellow, Plate IV, to an outer zone gradually stained Light Jasper Red, Plate XIII, to Jasper Red, Plate XIII, at margin edge; inside surface: Lemon Chrome, Plate IV, in small, well-defined base. Most of the petal is a bright Rose Red, Plate XII, tending toward Spectrum Red, Plate I, toward the base of the petal. Inner petal—outside surface: Baryta Yellow, Plate IV, stained Light Jasper Red, Plate XIII, along the outer edges; inside surface: has a small, well-defined zone of Lemon Chrome, Plate IV, at the base of the petal. From the yellow zone upward, the color shades evenly from Spectrum Red, Plate I, to Rose Red, Plate XII.

At some seasons of the year, outdoor blooms may have a little less of the red coloring, showing little or none of it on the outside of the petals and with the inside petal colors ranging from Peach Red, Plate I, to Strawberry Pink, Plate I, on outer and intermediate petals and on the inside petals, from Strawberry Pink, Plate I, to Light Strawberry Pink, Plate I, to Orient Pink, Plate II, near edges.

This description was made from a rose that was open for three days in a greenhouse in the month of March, at West Grove, Pennsylvania, U. S. A.:

*Color.*—Outer petal—outside surface: Baryta Yellow, Plate IV, shading to Picric Yellow, Plate IV, to Lemon Yellow, Plate IV, at center of base. Around the outer edges of the petals, there is a faint suggestion of a pink suffusion as if the inside petal color were showing through; inside surface: outer edge of Geranium Pink, Plate I (sometimes tinged with Rose Color, Plate XII, in some petals) to Rose Doree, Plate I. Toward the base, there is a golden glow over the Rose Doree, producing a glowing Strawberry Pink, Plate I. Below this there is a contrasting base zone of Lemon Yellow, Plate IV. Inner petal—outside surface: Baryta Yellow, Plate IV, shading to Picric Yellow, Plate IV, to Lemon Yellow, Plate IV, at center of base. The suggestion of pink suffusion around the outer margin of the petals is less and narrower than for the outer petals; inside surface: bright iridescent Rose Doree, Plate I, at outer tip, sometimes shading toward Rose Color, Plate XII, or Rose Pink, Plate XII, or even to Jasper Pink, Plate XIII, shading gradually to Strawberry Pink, Plate I, with a golden glow that increases toward the base. At the base is a contrasting zone of Pale Lemon Yellow, Plate IV, to deep Lemon Yellow, Plate IV, through the center. When petals are removed from this flower for study, they quickly darken. Color comparisons must therefore be made rapidly or they are not true.

*General color effect.*—Newly opened flower—Rose Red, Plate XII, (or lighter and yellower in some blooms at some seasons, to Peach Red, Plate I, or even Strawberry Pink, Plate I), with Baryta Yellow, Plate IV, reverse. Three days open—Rose Doree, Plate I, (or lighter or rosier in some blooms at some seasons), with a luminous golden glow and rich Lemon Yellow, Plate IV, center.

*Reproductive organs*

Stamens: Many; arranged irregularly about pistils; mixed with a few petaloids.
Filaments: Many with anthers; medium length. Color—yellow.
Anthers: Medium small; occasionaly an anther fused with a petaloid. Color—yellow.
Pistils: Many.
Styles: Uneven; medium weight; bunched. Color—rich pink.
Stigma: Color—very pale yellow.
Ovaries: All enclosed in calyx.

*Plant*

Foliage:

*Leaves.*—Compound of 3, 5 or 7 leaflets; abundant; medium-large; heavy; leathery; very glossy.

*Leaflets.*—Shape—ovate, with apex acuminate. Base—rounded; sometimes more or less cordate. Margin—simply serrate.

*Color.*—Mature—upper surface: very dark shining green; Danube Green, Plate XXXII, but shiny; under surface: Light Elm Green, Plate XVII. Young—upper surface: Hellebore Green, Plate XVII, but shiny and with veins tinged red to Mummy Brown, Plate XV, with more red on very young leaves; under surface: mixture of green, brown and red; the younger the leaf, the more red, then acquiring green with age.

*Rachis.*—Medium weight. Upper side—grooved. Under side—extremely thorny.

*Stipules.*—Medium length; medium narrow; with medium length points turning out at an angle of less than 45°.

*Disease.*—Resistant to mildew and blackspot, as determined by comparison with other varieties grown under comparable conditions.

Growth:

*Habit.*—Bushy; upright; much-branched.

*Growth.*—Moderate.

*Canes.*—Moderately heavy.

*Main stems.*—Color—green. Thorns—Many; long; fairly straight; with medium length oval base. Prickles—none. Hairs—none.

*Branches.*—Color—green to green-brown. Thorns—many; medium to long; fairly straight; with medium length oval base. Prickles—none. Hairs—none.

*New shoots.*—Color—green. Thorns—several; long; straight; with narrow base. Prickles—none. Hairs—none.

I claim:

A new and distinct variety of rose plant of the hybrid tea class, substantially as herein shown and described, characterized particularly as a novelty by the relatively vivid, lively, yet harmonious shades of red and yellow colors of its bi-colored blooms, combined with its superior foliage and good disease resistance, and the improved vigor of the plant as evidenced by its bushy habit of growth, production of foliage in abundance and great freedom of bloom.

FRANCIS MEILLAND.

No references cited.